(12) United States Patent
Larson et al.

(10) Patent No.: US 7,014,608 B2
(45) Date of Patent: Mar. 21, 2006

(54) GUIDED RETRACTOR AND METHODS OF USE

(75) Inventors: Jeffrey Larson, Spokane, WA (US); Theodore Bertele, Longmont, CO (US); Louis Greenberg, Boulder, CO (US); Scott Schorer, Niwot, CO (US)

(73) Assignee: Synthes Spine Company, LP, Paoli, PA (US)

( * ) Notice: Subject to any disclaimer, the term of this patent is extended or adjusted under 35 U.S.C. 154(b) by 19 days.

(21) Appl. No.: 10/734,546

(22) Filed: Dec. 12, 2003

(65) Prior Publication Data

US 2005/0038440 A1 Feb. 17, 2005

Related U.S. Application Data

(63) Continuation-in-part of application No. 10/645,136, filed on Aug. 20, 2003.

(60) Provisional application No. 60/433,343, filed on Dec. 13, 2002.

(51) Int. Cl.
*A61B 1/32* (2006.01)
(52) U.S. Cl. ..................................................... 600/201
(58) Field of Classification Search ................ 600/201, 600/204, 206, 208, 210, 219, 221, 235, 245; 606/53, 105, 119, 61, 86
See application file for complete search history.

(56) References Cited

U.S. PATENT DOCUMENTS

| 2,670,731 A | 3/1954 | Zoll et al. |
| 3,227,156 A | 1/1966 | Gauther |
| 3,749,088 A | 7/1973 | Kohlmann |
| 3,807,393 A | 4/1974 | McDonald |
| 4,765,311 A | 8/1988 | Kulik et al. |
| 4,817,587 A | 4/1989 | Janese |
| 4,913,134 A | 4/1990 | Luque |
| 4,950,270 A | 8/1990 | Bowman et al. |
| 4,984,564 A | 1/1991 | Yuen |
| 5,027,793 A | 7/1991 | Engelhardt et al. |
| 5,052,373 A | 10/1991 | Michelson |
| 5,125,396 A | 6/1992 | Ray |
| 5,303,694 A | 4/1994 | Mikhail |
| 5,503,617 A | 4/1996 | Jako |
| 5,707,390 A | 1/1998 | Bonutti |
| 5,728,046 A | 3/1998 | Mayer et al. |

(Continued)

FOREIGN PATENT DOCUMENTS

DE 40 28 651 A1 3/1992

(Continued)

*Primary Examiner*—Pedro Philogene
(74) *Attorney, Agent, or Firm*—Jones Day

(57) ABSTRACT

The present invention provides methods and apparatus in which a surgical retractor comprises a plurality of mechanically coupled tissue retaining walls that are guided into position along one or more guides previously implanted into the patient. The walls are preferably coupled by pivots, so that separating some of the walls from one another opens an operating space. There are preferably two guides, which are driven or screwed into the pedicles of vertebrae, or other bone. Since practical considerations will usually mean that the guides are not generally parallel to one another, the guides are capable of polyaxial movement with respect to the pedicles, and retractor is provided with oversized channels to receive the guides. The channels may be conveniently disposed in a frame, which also serves to hold lock the walls apart. Various convenience features are contemplated including a web disposed between the walls, which expands as the walls are separated. Also contemplated are projections from near the bottoms of one or more of the walls, which can alternatively or additionally help to hold the underlying tissue in place.

16 Claims, 3 Drawing Sheets

U.S. PATENT DOCUMENTS

| | | | |
|---|---|---|---|
| 5,730,757 | A | 3/1998 | Benetti et al. |
| 5,795,291 | A | 8/1998 | Koros et al. |
| 5,928,139 | A | 7/1999 | Koros et al. |
| 5,944,658 | A | 8/1999 | Koros et al. |
| 5,951,466 | A | 9/1999 | Segermark et al. |
| 5,954,635 | A | 9/1999 | Foley et al. |
| 6,007,487 | A * | 12/1999 | Foley et al. ................ 600/235 |
| 6,030,340 | A | 2/2000 | Maffei et al. |
| 6,063,088 | A | 5/2000 | Winslow |
| 6,083,154 | A | 7/2000 | Liu et al. |
| 6,090,113 | A | 7/2000 | Le Couedic et al. |
| 6,162,172 | A | 12/2000 | Cosgrove et al. |
| 6,187,000 | B1 | 2/2001 | Davison et al. |
| 6,206,826 | B1 | 3/2001 | Mathews et al. |
| 6,235,028 | B1 | 5/2001 | Brumfield et al. |
| 6,354,995 | B1 * | 3/2002 | Hoftman et al. ............ 600/219 |
| 6,394,950 | B1 | 5/2002 | Weiss |
| 6,416,518 | B1 | 7/2002 | DeMayo |
| 6,468,207 | B1 | 10/2002 | Fowler, Jr. |
| 6,488,620 | B1 | 12/2002 | Segermark et al. |
| 6,520,907 | B1 | 2/2003 | Foley et al. |
| 6,530,926 | B1 | 3/2003 | Davison |
| 6,537,323 | B1 | 3/2003 | Weinstein et al. |
| 6,596,008 | B1 | 7/2003 | Kambin |
| 6,616,605 | B1 | 9/2003 | Wright et al. |
| 6,676,665 | B1 | 1/2004 | Foley et al. |
| 6,746,396 | B1 | 6/2004 | Segermark et al. |
| 6,800,084 | B1 | 10/2004 | Davison et al. |
| 6,811,558 | B1 | 11/2004 | Davison et al. |
| 6,849,064 | B1 * | 2/2005 | Hamada ................ 604/164.01 |
| 2002/0111538 | A1 | 8/2002 | Wright et al. |
| 2002/0123668 | A1 | 9/2002 | Ritland |
| 2003/0073998 | A1 | 4/2003 | Pagliuca et al. |
| 2003/0139648 | A1 | 7/2003 | Foley et al. |
| 2003/0149341 | A1 | 8/2003 | Clifton |
| 2003/0191371 | A1 | 10/2003 | Smith et al. |
| 2003/0199871 | A1 | 10/2003 | Foley et al. |
| 2003/0236447 | A1 * | 12/2003 | Ritland ..................... 600/210 |
| 2004/0002629 | A1 | 1/2004 | Branch et al. |
| 2004/0059193 | A1 | 3/2004 | Famous |
| 2004/0059339 | A1 | 3/2004 | Rochm, III et al. |
| 2004/0138534 | A1 | 7/2004 | Ritland |
| 2004/0181231 | A1 | 9/2004 | Emstad et al. |
| 2004/0186346 | A1 * | 9/2004 | Smith et al. ................ 600/102 |
| 2004/0215199 | A1 | 10/2004 | Zinkel |
| 2004/0236317 | A1 | 11/2004 | Davison |
| 2004/0236331 | A1 | 11/2004 | Michelson |
| 2005/0010293 | A1 | 1/2005 | Zucherman et al. |
| 2005/0070765 | A1 | 3/2005 | Abelgany et al. |
| 2005/0080418 | A1 * | 4/2005 | Simonson et al. ............ 606/61 |
| 2005/0090899 | A1 | 4/2005 | DiPoto |

FOREIGN PATENT DOCUMENTS

| | | |
|---|---|---|
| EP | 0 455 282 B1 | 11/1991 |
| EP | 0 792 620 A2 | 3/1997 |
| EP | 1 192 905 A1 | 4/2002 |
| FR | 2 692 468 | 12/1993 |
| WO | WO 96/02195 | 2/1996 |
| WO | WO 98/12960 | 4/1998 |

* cited by examiner

FIG. 3
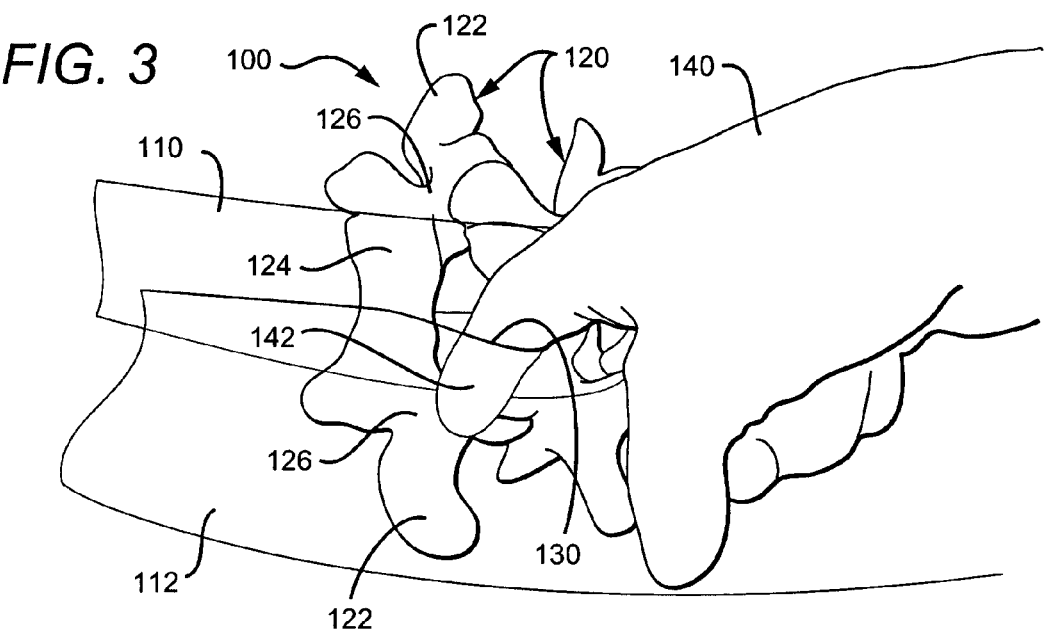
FIG. 4
FIG. 5
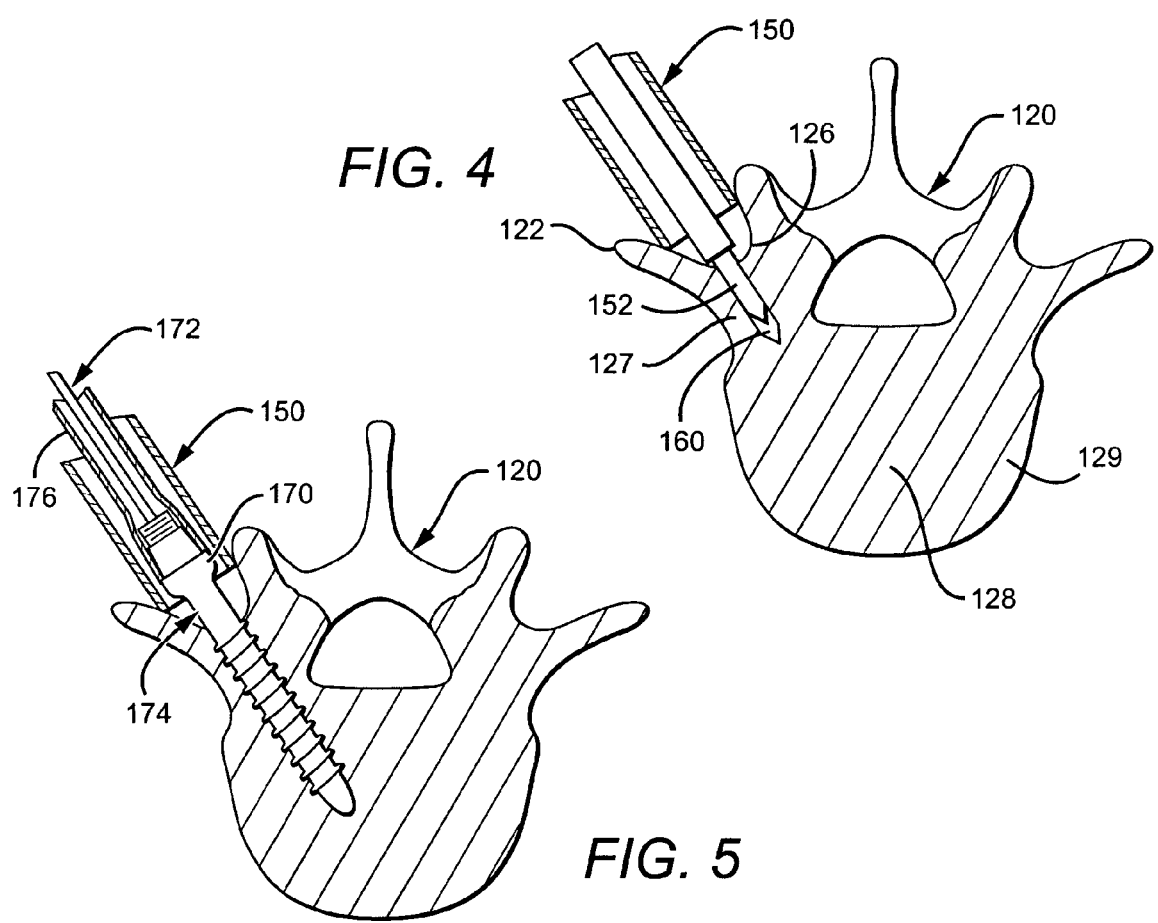

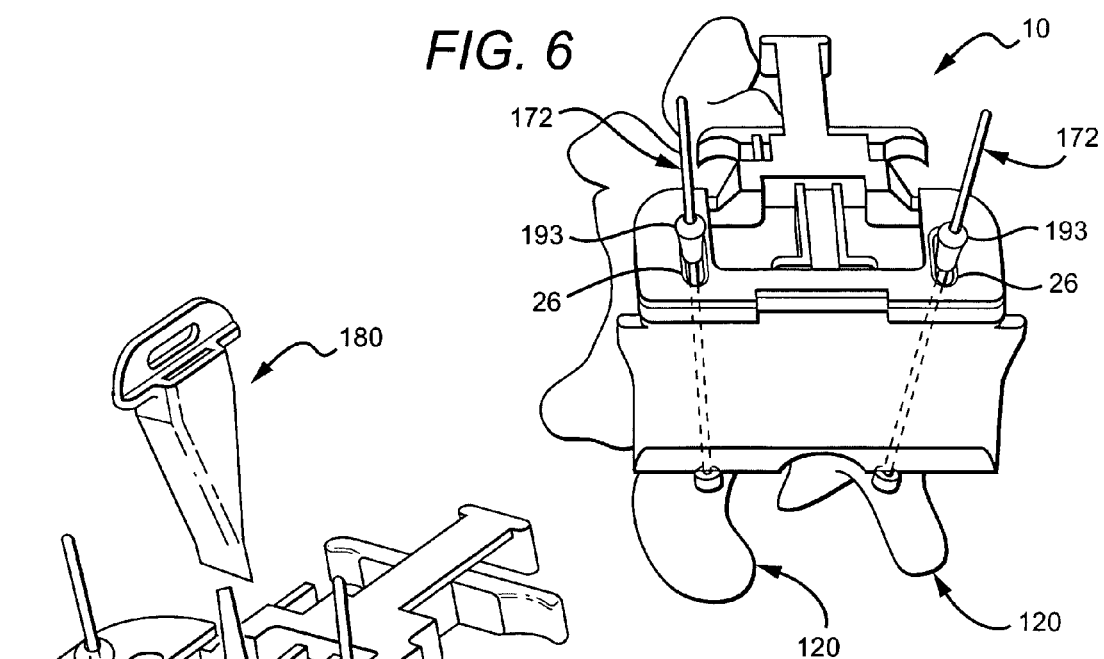
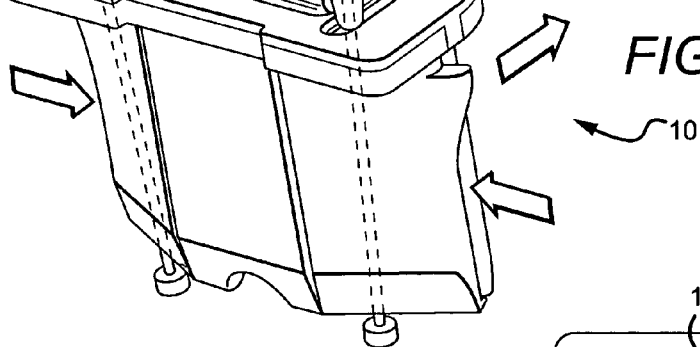
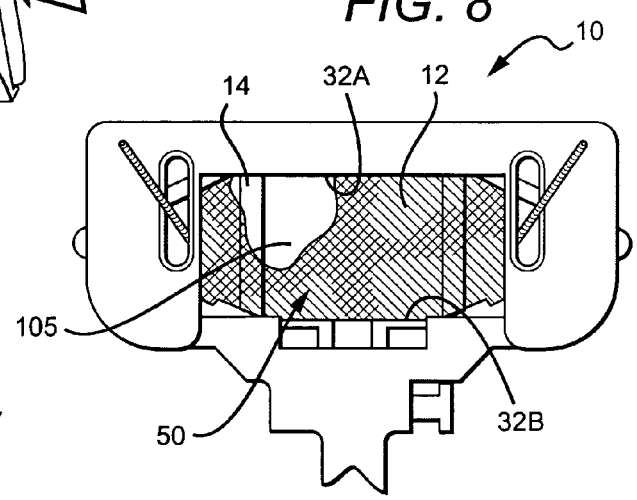
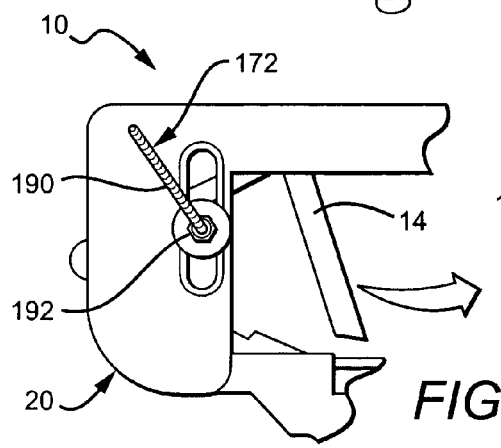

GUIDED RETRACTOR AND METHODS OF USE

CROSS REFERENCE TO RELATED APPLICATIONS

This is a continuation-in-part of application Ser. No. 10/645,136, filed Aug. 20, 2003, entitled "Guided Retractor and Methods of Use," which claims priority to Provisional Application Ser. No. 60/433,343, filed on Dec. 13, 2002, and incorporates both applications herein in their entirety and claims priority thereto.

BACKGROUND OF THE INVENTION

1. The Field of the Invention

The field of the invention is surgical retractors.

2. The Relevant Technology

Many types of surgical retractors are known. The simplest devices are tubular probes, or probes adapted with a paddle or other somewhat flatter surface. Recent embodiments of that concept are depicted in U.S. Pat. No. 6,206,826 to Mathews et al. (March 2001). More complicated retractors utilize scissors, bow string, or screw-jack expanders that operate against mating paddles. Those retractors have the advantage of being able to lock the paddles in place, leaving at least one of the surgeon's hands free for other actions. See e.g., U.S. Pat. No. 6,471,644 to Sidor (October 2002). Still other retractors are self opening, including Cosgrove et al., U.S. Pat. No. 6,162,172 (December 2000). All cited patents herein are incorporated herein by reference.

While undoubtedly useful in many respects, none of the above-mentioned retractors are readily fixed in position relative to one or more bones. U.S. Pat. No. 5,027,793 to Engelhardt et al. (July 1991) addresses that need to some extent, by providing spikes on the bottom of a retractor wall, and further providing spikes that can be driven into the bone. The contemplated use is to resect the operating area down to the bone, position the retractor, and then pound both the retractor and the spikes into place.

A problem remains, however, in that the resection required to properly position the retractor can cause considerable trauma to the overlying and surrounding tissues. Another problem is that multiple retractors are needed to retain tissue pushing into the operating area from different directions. The Engelhardt et al. retractor, for example, did not have to address that tissue because the preferred application was acetabular surgery, in which the major encroachment was from gluteus muscles that are all substantially superior to the operating site.

In spinal and some other surgeries these problems can be especially severe. Thus, there is still a need to provide methods and apparatus in which an operating space can be positioned and opened with respect to specific anatomical areas, while reducing trauma to surrounding tissue.

BRIEF SUMMARY OF THE INVENTION

To that end the present invention provides methods and apparatus in which a surgical retractor comprises a plurality of mechanically coupled tissue retaining walls, which are guided into position along one or more guides previously implanted into the patient.

Preferred embodiments utilize two main walls, and four smaller walls, one on each of the ends of the two main walls. In such embodiments all of the walls are coupled by pivots, such that the faces of the two main walls can be moved towards or apart from each other to open or close an operating space. The faces of at least the main walls are preferably flat, but can be any other suitable shape, including convex. The invention is particularly suited for operating on or near curved bony surfaces, and the bottoms of the walls can be compliant (i.e., advantageously adapted to fit and/or conform to the bone surface below).

There are preferably two guides, which are driven or screwed into the pedicles of vertebrae, or other bone. The various guides can be implanted into different bones, or different areas of the same bone. Since practical considerations will usually mean that the guides are not parallel to one another, the retractor has oversized channels to receive the guides, and the guides should be polyaxially moveable relative to the pedicles. The channels can be circular in cross section, but are more preferably elongated into an oblong or other slotted shape.

The channels are best disposed in a frame, which also serves to hold lock the walls apart. Any suitable devices can be used to move apart the main walls to open the operating space, including for example a simple wedge or T-bar, or a mechanism disposed on the frame. The frame can be held in place relative to the guides by wires, nuts, clamps, and so forth.

Various convenience features are contemplated including a web disposed between the walls, which expands as the walls are separated. The web can be cut, torn, bent away, or otherwise manipulated to expose the tissue below. Also contemplated are projections from near the bottoms of one or more of the walls, which can alternatively or additionally help to hold the underlying tissue in place, and can similarly be removed in any suitable manner from the corresponding wall. The frame or other position of the refractor can be transparent to aid in surgeon visualization.

These and other objects and features of the present invention will become more fully apparent from the following description and appended claims, or may be learned by the practice of the invention as set forth hereinafter.

BRIEF DESCRIPTION OF THE DRAWING

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 3 is a perspective view of the back and spine of a patient, in which finger dissection is being employed to locate a pedicle of a vertebra.

FIG. 4 is a horizontal cross-sectional view of a vertebra, showing use of an awl to punch a guide hole into a pedicle.

FIG. 5 is a horizontal cross-sectional view of the vertebra of FIG. 4, in which a screw is being screwed into the hole created in FIG. 4.

FIG. 6 is a perspective view of the back and spine of a patient in which the closed retractor of FIG. 2 is being fitted onto the guides implanted into adjacent vertebrae.

FIG. 7 is a perspective view of the back and spine of the patient of FIG. 6 in which the retractor is being opened by an opening tool.

FIG. 8 is a perspective view of the back and spine of the patient of FIG. 6 in which the retractor has been opened, and the web is being removed to expose various fingers and the underlying tissue.

FIG. 9 is a perspective view of the back and spine of the patient of FIG. 6 in which the retractor has been opened, and various fingers (bottom tissue retainers) are being removed.

DETAILED DESCRIPTION

The present invention is directed to a new surgical retractor and related methods that permit a surgeon to establish a useful operating space while at the same time reducing the amount of trauma to surrounding tissue in comparison to alternatives.

This is accomplished by providing a retractor system that is preferably substantially linear in form when in the closed state, by which it is meant that when in a closed position it has an aspect ratio that is substantially wider than it is thick when viewed from above. This permits it to be placed in the area to be retracted relatively easily, and leads to formation of a useful operating area when it is moved to an open position.

A presently preferred use for the inventive retractor is in connection with lumbar surgery, and the following discussion shall use that as an example. It should be understood, however, that the apparatus and methods of the present invention could be applied to other uses with beneficial results.

Figure 1:
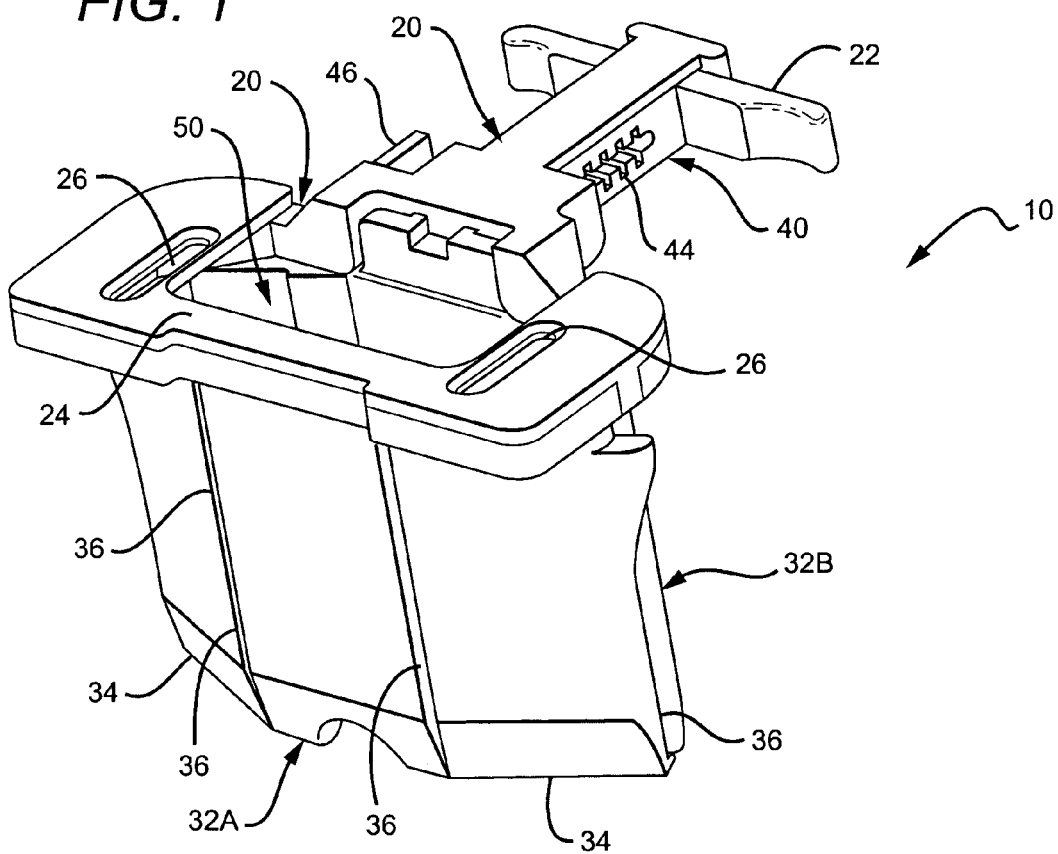
FIG. 1 is a perspective view of a retractor according to the inventive subject matter, in an open configuration.

FIG. 1 generally depicts a retractor 10, having a frame 20, which serves as a retractor body. In the embodiment of FIG. 1, retractor 10 is provided with major walls 32A, 32B and minor walls 34, which are coupled together by six hinges 36. FIG. 1 depicts retractor 10 in an open position, which defines an operating space 50. A locking/opening mechanism 40 is provided to maintain the retractor at the desired open position.

The frame 20 can be any suitable size and shape according to a particular application, with larger frames being generally more useful for larger incisions. For posterior lumbar surgery on adult humans, the overall dimensions of the presently preferred frame are about 5.5 cm in depth, 3.5 cm in length, 3.0 cm in width. Frame 20 can be made of any suitable material, especially a nontoxic polymer such as polyethylene. The frame 20 can advantageously be colored to reduce glare from operating room lighting, and some or all of the frame can be relatively transparent.

Frame 20 may include a handle portion 22 in association with the locking mechanism 40, and a perimeter 24 around the operating space 50. The locking mechanism 40 is shown as a ratchet structure, but it will be appreciated that other locking mechanisms could be used, especially those that provide for a high degree of reliability and ease of operation. In the illustrated embodiment, at least one of the walls 32A, 32B, 34 is preferably coupled to the perimeter 24, such as through use of a pin (not shown).

Channels 26 are located on opposite sides of the perimeter 24, and are each sized to receive one of the guides 172 (see FIGS. 4–9). The system is designed to work with a wide range of pedicle screw or other bone fixation systems, and with various numbers of guides, regardless of the specific relationship between screw and guide. It is preferred that the passageways defined by the channels 26 be oversized with respect to the outside diameters of the shafts of the guides 172 so that the channels 26 can easily receive guides 172 that are out of parallel or in some other manner not perfectly aligned with each other and/or with the channels. In a preferred embodiment, the channels define a passageway having a diameter of about 5 to 15 mm, whereas the guides 172 (see FIGS. 5, 6) preferably have a corresponding diameter of about 4 to 6 mm. All ranges set forth herein should be interpreted as inclusive of the endpoints.

As with other components, the various walls 32A, 32B, 34 are preferably made of a biocompatible material, and here again they can have any suitable sizes and shapes, depending on the surgical site or sites for which they are intended. Walls 32A, 32B, 34, for example, can be mostly rectangular in vertical cross-section as shown, with bottoms of at least the major walls 32A, 32B curved to accommodate specific bone shapes, such as that of the laminae of the vertebrae in spinal surgery. It is also contemplated that the bottoms of at least the major walls 32A, 32B can be pliable, to conform at least partially to projections and depressions of the underlying bone. Walls 32A, 32B, 34 are depicted in the figures as having flat sides, but alternatives may be bowed outwardly (convex), inwardly (concave), or may have any other suitable horizontal cross-section.

One or more of the walls (not shown) can even be inflatable, made out of balloons that define the opening. Of course, the walls 32A, 32B, 34 must be sturdy enough, and therefore thick enough, to withstand the expected forces placed upon them. The walls 32A, 32B, 34 are preferably not so thin that they would cut into the tissue below during deployment, yet they should not be so thick as to significantly interfere with the size of the operating area. A presently preferred thickness in connection with the illustrated embodiment is from about 3.5 mm to about 5 mm at the thickest point, tapering down to a thickness of about 1.5 mm–3 mm at the bottom of each wall. The walls can also be nested in any suitable manner, which simply means that a portion of one wall may extend around a portion of another wall.

The hinges 36 are shown in the illustrated embodiment as continuations of the walls 32A, 32B, 34. Indeed all of the walls and hinges can be molded as a single piece, with each of the hinges 36 being formed as an especially thin region of a wall. This type of hinge is a so-called "living hinge" that can handle multiple openings when formed of a suitable material such as polypropylene. It will be appreciated that other configurations of hinges may be used. For example, instead of four minor walls 34, the major walls 32A, 32B could be coupled by only a single outwardly bowed, flexible piece (not shown) at each end. Certainly the total number of walls can be greater or less than 6.

The term "wall" is used herein in a very broad sense, to mean any sort of tissue retaining barrier, generally wider than thick, and having a useful height for an intended use. The sides of the walls may be pitted or indented as would occur if the sides had a mesh coating (not shown), and the sides may even have through holes (not shown).

Because the closed form of the illustrated embodiment is rather linear in shape when viewed from the perspective of the area to be retracted, the illustrated embodiment of retractor 10 may be referred to as a "linear retractor" to distinguish it from point retractors that are basically circular tubes. This term does not mean that the retractor as a whole nor any of the walls are necessarily linear, nor does the term mean that the wall is so thin as to constitute a cutting blade. A feature of the use of a linear retractor as illustrated is that the walls have substantially the same circumference in both the closed and open positions, and the design and placement of the "living hinges" control the shape of the operating area during retraction. This design is believed to have a number of advantages, including the distribution of pressure along the tissue to be retracted, a closed operating space of controllable size and shape, and a relatively wide operating space that allows a surgeon to have direct visualization of the surgical area as well as room to manipulate the surgical instruments.

Locking/opening mechanism 40 is shown as a typical ratcheting type mechanism, with teeth 44, and having a release 46. Frame 20 can have both a locking mechanism and an opening mechanism (not shown), or either one by itself. There are numerous other locking and/or opening mechanisms known to the field, and presumably others will become known in the future. It is contemplated that any suitable locking and/or opening mechanisms can be used.

Operating space 50 will be larger or smaller depending on the sizes and shapes of the walls, and the extent to which the walls are separated out from one another. A preferred area of the operating space 50 for lumbar surgery is in the range of about 7 cm$^2$ and 14 cm$^2$.

Figure 2:
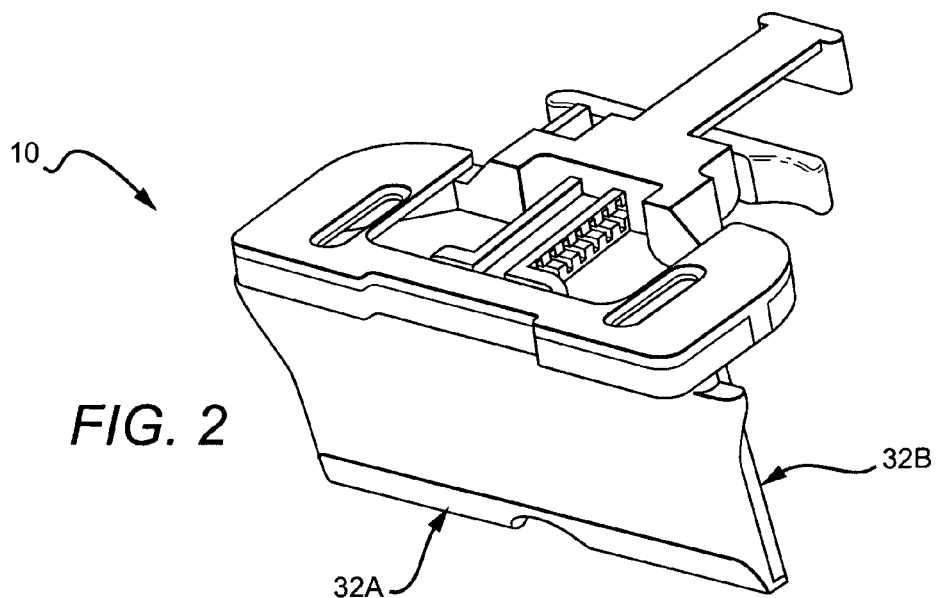
FIG. 2 is a perspective view of the retractor of FIG. 1, disposed in a closed configuration.

FIG. 2 generally depicts the retractor 10 of FIG. 1 disposed in a closed configuration. The terms "closed" and "open" with respect to configurations of the retractor 10 are relative. Thus, closed merely means substantially closed, but does not require complete closure, so that the walls 32A, 32B are juxtaposed. In a closed position the walls 32A, 32B may well be separated by up to 1 mm or more. Similarly, in a contemplated open configuration, walls 32A, 32B would likely be separated by at least 1.5 cm, but may be separated by up to 2.3 cm or more, depending upon the intended use.

FIG. 3 generally depicts a portion of the spine 100 of a patient, in which the paraspinous muscles are designated schematically by semitransparent bands 110, 112, respectively. The spine 100 includes vertebrae 120, each of which includes transverse processes 122, spinous processes 124, and pedicles 126. An incision 130 has been made, and a finger 142 of hand 140 is being used to dissect through the muscle and locate one of the pedicles 126. Of course a wedge, probe or other tool could be used in place of or in addition to the finger 142 to locate the pedicles.

FIG. 4 generally depicts cannula 150 that positions an awl 152 or a probe for use in producing a hole 160 in pedicle 126. The awl 152 can be manually pushed or otherwise forced through the cortex 127 of the pedicle. Cannula 150 is preferably made of radiolucent material such as plastic or carbon fiber, while awl 152, and other tool attachments and inserts are all preferably made of metal such as surgical steel, titanium, or other durable, radio opaque material. Positioning the cannula 150 can be aided by fluoroscopy or other visualization technique.

In preferred methods, the awl 152 is withdrawn, and a longer, thinner probe (not shown) is inserted through the pedicle 126 into the softer medulla 128 of the body 129 of the vertebra 120. The longer probe is then withdrawn, and in FIG. 5 a screwdriver 176 is shown in use to insert a screw 174. The illustrated screw is provided with a head 170, which holds a guide 172 in place. The screwdriver 176 is then removed, leaving the screw 174 implanted into the vertebra 120, and guide 172 attached to the top of screw 174 in a polyaxial engagement, by which it is meant that the guide is free to move in an area that defines a cone emanating from the point of attachment to the end of the screw, and with the axis of the cone being coaxial with the longitudinal axis of the screw. This process is repeated to insert another screw and associated guide 172 into another area of bone, which in the case of spinal surgery is most likely the pedicle of an immediately superior or inferior vertebra on the same side. In other surgeries (not shown), the second, or possibly even a further guide, can be inserted into a different location of the same bone as received the first guide.

In FIG. 6 the guides 172 that are implanted into adjacent vertebrae 120 have been inserted into the channels 26 of the closed retractor 10. The polyaxial movement of the guides and the oversize width of the channels make it a simple matter to insert the guides through channels 26 even if the width of the channels do not correspond perfectly to the width between the adjacent pedicles, or if the screws are not oriented parallel to one another. Those skilled in the art will realize that the channels can have other configurations besides those shown in the drawing, and can be multi-level rather than simply 1-level.

FIGS. 8 and 9 show that the guides may be provided with threads 190 that receive wing nuts or other correspondingly threaded pieces 192 that assist in anchoring the frame 20 to the guides 172. In alternative configurations one could use non-threaded lock down pieces such as finger clamps 193. Yet another alternative would be to place a template (not shown) on top of the frame, and the template may be held in place using the wing nuts, finger clamps, or other hold-down devices. The frame can also be used to hold additional devices, such as suction or lighting, introduced into the field 50 and held in place by a coupling device on the frame 20. It will be appreciated that the guides need to be long enough to permit them to extend sufficiently through the channels to allow them to receive the appropriate hold-down device so that the retractor body may be pulled down onto the end of the associated pedicle screw.

In FIG. 7 the retractor 10 is shown in the step of being opened by an expander 180, which may be manually inserted between the opposing walls to produce and widen a gap between them. In this figure the expander generally comprises a wedge with a handle. The expander 180 may be preferable over using unassisted fingers because it involves a mechanical advantage. Alternatively, the retractor can be opened using fingers, such as by using a thumb and fingers-opposing force method using the handle 22 and frame 20. There are numerous alternatives which may or may not involve any mechanical advantage, including for example a T-shaped handle coupled to a shaft and a cam (not shown).

In order to minimize damage to the tissues in the area of a lumbar operation, it is desired for some procedures that the retractor be opened to provide a working area that is greater than, but only slightly greater than, the distance between corresponding adjacent pedicles. It should be understood, however, that one could open the retractor to a distance less than the distance between corresponding adjacent pedicles, and the retractor may be designed to be opened to a greater extend than the pedicle to pedicle distance. Retractor 10 should be configured so as to allow it to be opened large enough to form a desired operating space. Optionally, the retractor may be configured to prevent it from being overly-expanded. If desired, various sizes of retractors might be provide so as to allow selection of the smallest possible retractor that will provide an adequate operating space.

In FIG. 8 the retractor 10 has been opened to reveal an optional web 12 positioned between walls 32A, 32B and 34. The web 12 is preferably a thin, flexible sheet of latex or other biocompatible plastic, which can be easily cut, ripped, or in some other manner disrupted to expose desired portions of underlying tissue 105 while keeping other tissue from intruding into the working space. Web 12 is shown as covering the entire floor of the operating space 50, but it could alternatively cover a lesser space, and could extend between or among different walls.

FIG. 8 also depicts the optional use of retaining fingers 14, which are depicted as extending from or rotating out below the web 12, although some or all of the fingers 14 could alternatively be positioned above the web 12. It is preferred that fingers 14 be formed from a malleable material so that they may be used to retract individual nerves, or other anatomical elements by being mechanically positioned by the surgeon.

In FIG. 9 the retractor 10 is shown in an open position, and various unwanted fingers 14 are depicted as being removed from the operating space. Such removal can be accomplished in any suitable manner, including by cutting (as with a scalpel or scissors), bending by hand or with a tool, and so forth. There may be wide fingers, narrow fingers, long or short fingers, closely spaced or widely spaced fingers, flat or rounded fingers, or in other configurations that might be useful for an intended use. Where fingers are used, they may be molded as continuous extensions of the walls or they may be secured to the walls in some fashion. It would also be possible to take a malleable material and coat it with the material of the walls, thereby integrating them into the walls while making them available for retraction of individual feature in the operating region.

Preferred methods of inserting a tissue retractor 10 into a patient involve the steps of providing a retractor 10 having paired tissue retracting surfaces (such as on walls 32A, 32B, 34) and first and second guide receiving areas (such as channels 26); percutaneously or otherwise implanting first and second guides (such as guides 172) into different areas of bone in the patient; then positioning upper ends of the first and second guides through the first and second guide receiving areas, respectively, then fully inserting the retractor down the guides and into the patient, effectively splitting the muscle; and finally moving the tissue retracting surfaces apart from one another to open the operating space. These methods are especially useful where one or more of the guides are screws, which are implanted into very specific anatomical structures such as the pedicles of vertebrae. The contemplated methods are also extremely useful in opening operating spaces overlying adjacent bones. Especially preferred methods optionally employ nuts, clamps, or other readily attachable and securable mechanisms to stabilize the retractor 10 on the guides and/or to pull the retractor down onto the end of the associated pedicle screw.

From the description above, it should now be apparent that the novel methods and apparatus disclosed herein turn the normal retracting procedure on its head. Instead of positioning the retaining wall or walls and then holding them in place by implanting spikes or posts into the bone, as was done prior to the present invention, the present procedure implants guides, and then uses them to position the retractor. Of course, it would be possible to position the retractor first, and then place the guides, and the present invention provides useful improvements for this alternative method.

The advantages of turning the procedure around are significant. Among other things, this new procedure allows the surgeon to exactly position the retractor 10 at the intended operative site because the positioning can be done precisely with respect to underlying bony structures (e.g., the pedicle 126 of a vertebra). The screws are implanted where the surgeon wants them, and the guides 172, being attached to the top of the screws guide the retractor down into the desired anatomy, splitting the muscles, and defining a operating site 50 within the walls 32A, 32B and 34. After that the operating site 50 is opened, giving the surgeon the desired exposure needed to conduct the surgery without excess retraction and resulting tissue destruction.

Another advantage is that these new methods and apparatus speed up the procedure and makes more efficient use of resources relative to the prior art. Among other things, after the guides 172 and screws 174 are placed and the retractor 10 is attached and opened, there is no more need for fluoroscopy, which can be moved along to a different room.

Another advantage arises from the use of a linear retractor. A thin but wide device, when in the closed position, has been found to be easily placed in the operative region, and because it splits anatomical features, such as muscles, along a line, it provides a very useful operating space when in the open position. It is a feature of the present invention that the retractor is minimally invasive, yet provides an operating space that is large enough and has a useful shape that permits the surgeon to visually observe the operative site while performing the surgery. This is a marked improvement over tubular retractors.

Still other advantages involve convenience and reduction in surgeon stress. The novel methods and apparatus make it mentally easier on the surgeon. After the screws 174 are in, in the first part of the procedure, everything else in terms of opening the operating site is fairly straightforward. This helps the surgeon relax mentally and physically.

Thus, specific embodiments and applications of novel retractors have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A retractor system comprising:
   a. a retractor body having a closed position and an open position, said closed position presenting a substantially linear form for ease in placement of the closed retractor body in a region to be retracted, and said open position providing a working area that is greater than, but only slightly greater than, the distance between corresponding adjacent pedicles in said area to be retracted, and said retractor body having two elongated channels;
   b. a pair of pedicle screws for attachment to each of said correspondingly adjacent pedicles, and a pair of guide members in polyaxial engagement with a respective pedicle screw so that the guide members in polyaxial engagement with a respective pedicle screw so that the guide member has a range of movement defining a cone with respect to the longitudinal axis of said screw, each of said guide members having sufficient length to permit it to pass through a corresponding channel in the retractor body, and each guide member having an associated attachment member for use in urging the retractor body down onto the end of the associated pedicle screw; and
   c. said retractor body having a living hinge that allows movement from the closed position to the open position while fully enclosing said working area when in the open position, the perimeter of said retractor body being substantially the same in both the closed and the open positions.

2. A retractor system as defined in claim 1, further comprising a web across the bottom of the operating space when the retractor is in an open position, said web being formed of a material that can be removed in areas where desired but which can prevent unwanted tissue form intruding into the operating space in other areas.

3. A retractor system as defined in claim 1, further comprising at least one finger formed of a material that permits it to be used to retract anatomical elements within the operating field.

4. A retractor system comprising:
   a. a retractor body having a closed position and an open position, said closed position presenting a substantially linear form for ease in placement of the closed retractor body in a region to be retracted, and having two channels;
   b. a pair of pedicle screws for attachment to pedicles; and
   c. a pair of guide members in polyaxial engagement with a respective pedicle screw so that the guide member has a range of movement defining a cone with respect to the longitudinal axis of said screw, wherein each guide member extends through a channel.

5. A retractor system comprising:
   a. a retractor body having a closed position and an open position, the perimeter of said body being substantially the same in both the closed and open positions, said body including a plurality of hinges to permit it to move between said open and closed positions, and having two channels;
   b. a pair of pedicle screws for attachment to pedicles; and
   c. a pair of guide members in polyaxial engagement with a respective pedicle screw so that the guide member has a range of movement defining a cone with respect to the longitudinal axis of said screw, wherein each guide member extends through a channel.

6. A retractor system as defined in claim 5, wherein the retractor body is formed from a single piece.

7. The retractor system of claim 4, wherein at least a portion of the retractor body is substantially flat.

8. The retractor system of claim 4, wherein the retractor body has a living hinge.

9. The retractor system of claim 4, wherein the retractor body comprises a plurality of retractor walls.

10. The retractor system of claim 4, wherein the retractor body further comprises a frame.

11. The retractor system of claim 5, wherein at least a portion of the retractor body is substantially flat.

12. The retractor system of claim 5, wherein the retractor body further comprises a frame.

13. A retractor system comprising:
   a. a retractor body having a closed position, and an open position providing a working area that is greater than the distance between corresponding adjacent pedicles in said area to be retracted, and said retractor body having two elongated channels;
   b. a pair of pedicle screws for attachment to each of said correspondingly adjacent pedicles, and a pair of guide members in engagement with a respective pedicle screw, each of said guide members having sufficient length to permit it to pass through a corresponding channel in the retractor body; and
   c. said retractor body having a living hinge that allows movement from the closed position to the open position while fully enclosing said working area when in the open position, the perimeter of said retractor body being substantially the same in both the closed and the open positions.

14. The retractor system of claim 13, wherein the retractor body further comprises a frame.

15. The retractor system of claim 13, wherein a cross-sectional area of a guide member is substantially smaller than the size of its corresponding channel.

16. The retractor system of claim 13, further comprising a locking mechanism.

* * * * *